United States Patent [19]

McHardy

[11] 4,078,088

[45] Mar. 7, 1978

[54] METHOD OF TREATING THEILERIOSIS

[75] Inventor: Nicholas McHardy, Beckenham, England

[73] Assignee: Burroughs Wellcome Co., N.C.

[21] Appl. No.: 767,453

[22] Filed: Feb. 10, 1977

[30] Foreign Application Priority Data

Feb. 10, 1976 United Kingdom ............... 5100/76

[51] Int. Cl.$^2$ ............................................. A61K 31/12
[52] U.S. Cl. ................................................. 424/331
[58] Field of Search ....................................... 424/331

[56] References Cited

PUBLICATIONS

Berberian et al.-Chem. Abst. vol. 70, (1969), p. 10252t.

*Primary Examiner*—Sam Rosen
*Attorney, Agent, or Firm*—Donald Brown

[57] ABSTRACT

A method of treating Theileriosis in cattle and sheep both therapeutically and prophylactically, comprising the administration of an effective amount of a compound which is a 2-hydroxy-1,4-naphthoquinone derivative of formula (I) or a pharmaceutically acceptable salt thereof,

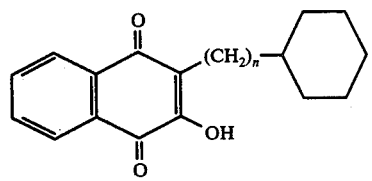

wherein *n* is zero or 1 to 12, as active ingredient, to an animal which is susceptible and infected with or potentially exposed to an infection with *Theileria* species.

15 Claims, No Drawings

METHOD OF TREATING THEILERIOSIS

The present invention relates to methods of treating and preventing theileriosis in cattle and sheep, and to preparations suitable for administration to these animals.

Theileriosis in cattle and sheep is a complex of diseases caused by protozoa of the species *Theileria*. The disease in cattle is caused either by *Theileria parva, Theileria lawrencei*, or *Theileria annulata* and is prevalent mainly in Central and East Africa and the Middle East. In sheep, it is *Theileria hirci* and *Theileria ovis* which cause the disease and this is prevalent in the Middle East. Infected ticks transmit the disease-causing parasite which on entering the mammalian host infects the lymphoid cells, which then proceed to divide rapidly. The parasite, therefore, stimulates normally non-dividing lymphocytes to divide and death is apparently caused by rupture of the lymphocytes with the release of toxic products, as well as by harmful effects of the parasites themselves. After release from the lymphocytes the parasite infects the erythrocytes and it is at this stage that ticks feeding on infected animals become themselves infected.

In the field there is no known effective treatment of theileriosis. The only drug that has hitherto been used for the treatment of cattle and sheep is oxytetracycline (Terramycin), the usual use of which is against anaplasmosis and bacterial infections. According to S. F. Barnett in Infectious Blood Diseases of Man and Animals, Vol. III Eds. Weinman D. & Ristic M., Academic Press 1968, this compound has had only very limited success when given before an injection is established, but no effect once the infection is actually established. Frequently, the symptoms of anaplasmosis are misinterpreted and theileriosis is diagnosed, and as a result oxytetracycline is administered, often in massive doses up to nearly the toxic level. Apparent recovery from theileriosis is in actual fact real recovery from anaplasmosis.

British patent specification No. 1,179,000 describes the preparation of 2-hydroxy-3-(8-cyclohexyloctyl) and 2-hydroxy-3-(7-cyclohexylheptyl)-1,4-naphthoquinone which have both been found to have antimalarial activity when tested in mice. 2-Hydroxy-3-(8-cyclohexyloctyl)-1,4-naphthoquinone, otherwise known as 'menoctone,' has been tested against malaria in humans but the results showed limited usefulness and consequently the drug was never marketed.

It has now been found that certain substituted naphthoquinones, in particular 2-hydroxy-3-(8-cyclohexyloctyl)-1,4-naphthoquinone and 2-hydroxy-3-cyclohexyl-1,4-naphthoquinone, show very good activity and are particularly effective in the treatment of theileriosis in cattle and sheep, in so much as they also allow the development of immunity to subsequent attacks of the disease, provided the dosage of active ingredient is within a predetermined specific range. Furthermore the 'sterilization' of animals, which are carriers of *Theileriosis annulata*, i.e., virtually complete eradication of the causative organisms in the host animal, can also be achieved under appropriate conditions. Moreover, the experimental investigations in the field have shown the possibility of prophylaxis in apparently healthy animals.

According to one aspect of the invention there is provided a method of treating theileriosis in cattle and sheep both therapeutically and prophylactically, comprising the administration of an effective amount of a compound of formula (I) or a salt thereof, especially in the form of a pharmaceutically acceptable salt,

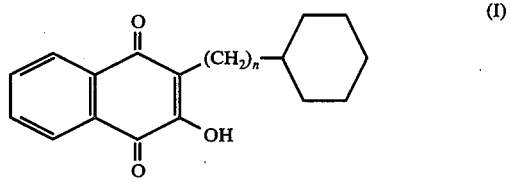

wherein $n$ is 0, or 1 to 12, as active ingredient, to an animal infected with, or potentially exposed to, an infection with *Theileria* species. The preferred compounds are those in which $n$ is less than 8. The most preferred compounds are 2-hydroxy-3-(8-cyclohexyloctyl)-1,4-naphthoquinone, otherwise known as 'menoctone' and 2-hydroxy-3-cyclohexyl-1,4-naphthoquinone, which have been found to be particularly active against theileriosis.

The preparation of the compounds of formula (I) may be carried out for instance by the process described in the above-mentioned British Pat. No. 1,179,000, and they may be converted to the salts by known methods.

Compounds wherein $n$ is 1 to 12 can therefore be prepared, for instance, by reacting a 2-(ω-cyclohexylalkyl)-1,4-naphthoquinone with hydrogen peroxide, under alkaline conditions to form the 2,3-oxide, which is then hydrolyzed under acidic conditions to produce the desired product. The 2-(ω-cyclohexylalkyl)-1,4-naphthoquinones may be prepared, for instance, by reaction of the corresponding 2-(ω-cyclohexylalkyl)-1-naphthols with chromium trioxide under acidic conditions, whilst the 2-(ω-cyclohexylalkyl)-1-naphthols may themselves be prepared, for example, by the interaction of 1-naphthol and the appropriate cyclohexanoic acid in the presence of boron trifluoride etherate. 2-Hydroxy-3-cyclohexyl-1,4-naphthoquinone, however, can be prepared by treating 2-hydroxy-1,4-naphthoquinone with hexahydrobenzoylperoxide as described in U.S. Pat. No. 2,553,647. 2-Hydroxy-1,4-naphthoquinone may be prepared, for example, according to the method described by Fieser, *J. Am. Chem. Soc.* (1948), 70, 3165.

For therapeutic treatment the compound of formula (I), or a salt thereof may be administered as one relatively large dose on the day the temperature of the animal rises and schizonts appear or later in the disease syndrome than this, followed by smaller daily doses for the next few days, for example 5 days. The total dosage over the treatment period is preferably from 1 to 20mg/kg active ingredient, more preferably 3 to 15mg/kg active ingredient, most preferably 5 to 10 mg/kg. The treatment may alternatively comprise a single dose or 2 doses administered on consecutive days, or could comprise up to a total of 10 doses. For instance, an effective single dose administered to a 200kg cow may comprise 1000mg which is given on day 1 followed by a daily dose of 200mg given on 5 consecutive days.

In prophylactic treatment, for example when an animal is suspected of having been exposed to infection, the compound of formula (I) may be administered for instance as a dose of 2.5mg/kg on the first day, followed by consecutive daily doses of 0.5mg/kg for up to 9 days, giving a total dose of 7mg/kg. Depending on the severity of the risk or exposure, daily doses of 0.2 to 5mg/kg may be administered. The duration of such preventative measure may last from 4 to 20 or even 120 days. Alternatively, the compound can be incorporated into a slow release chronic implant, which is formulated into a pellet with a relatively insoluble carrier, so that it can be injected under the skin by means of a gun. As the pellet dissolves the active ingredient is released slowly over a period of for example 4 months, so that a low level of protection is maintained, which is equivalent to the above regimen.

Compounds of formula (I) and their salts may be presented in association with a suitable carrier in pharmaceutical formulations for parenteral (sub-cutaneous or preferably intramuscular), intravenous or oral administration. A sterile injectable formulation is advantageously formed in an organic carrier, which may also contain bacteriostatic agents, antioxidants, buffers, solutes to render the preparation isotonic with the blood, thickening agents, suspending agents or other pharmaceutically acceptable additives.

The injectable formulations may be presented in unit-dose containers, such as ampoules, or disposable injection devices, or in multi-dose forms such as bottles from which an appropriate dose may be withdrawn.

The formulations for oral administration may include as carriers solids to form tablets, pastes, granules or powder, or may include liquids for suspensions or solutions, which may contain diluents, binding agents, dispersing agents, surface active agents, lubricating agents, coating materials, colouring agents, solvents, thickening agents, suspending agents or other pharmaceutically acceptable additives, and these preparations may be presented in unit dose form or multi-dose form, or as additives to foodstuffs. The compounds of formula (I) may also be formulated into a salt-lick so that the animals can obtain prophylactic treatment when in the field.

Compounds of formula (I) can also be formulated into a pour-on preparation containing for example up to 10% by weight active compound in a suitable carrier such as dimethylsulphoxide.

According to another aspect of the invention there is provided an anti-theileriosis composition comprising a compound of formula (I), as hereinbefore defined, or a pharmaceutically acceptable salt thereof, together with a pharmaceutically acceptable carrier therefor in effective unit dose form.

As used herein the term "effective unit dose" or "effective amount" is denoted to mean a predetermined anti-*theileria* amount sufficient to be effective against the protozoal organism in vivo.

A typical single dose for adult cattle weighing 400 kg may be 2000mg, whereas for calves it may be 500mg and for sheep 250mg.

In a further aspect of the invention there is provided an anti-theileriosis composition comprising a compound of formula (I), as hereinbefore defined or a pharmaceutically acceptable salt thereof, together with a pharmaceutically acceptable carrier therefor in effective unit dose form and instructions in the prophylactic treatment of theileriosis. These instructions explain the use and importance of the recommended doses in achieving the desired result. The instructions and pharmaceutical composition are packaged together in a box thereby forming a treatment pack.

The following examples illustrate the practice of the invention more particularly and the results obtained in field trials, but are not intended to limit the scope of the invention in any way.

EXAMPLE 1

Therapeutic Trial

A. Experimental animals

Fourteen grade jersey heifers about 6 months old were used. The were all serum negative when tested with *T. parva* (Muguga) schizont antigen, and weighed about 100 kg.

B. Methods of Observation

The course of the infection was monitored both by daily temperature, and by the examination of lymph-node smears, stained with Giemsa, taken from the right ear-node from day 5, and the left pre-scapular node from day 9. These smears were examined for the presence of macroschizonts and microschizonts. Blood smears were taken from day 9 and examined for the presence of erythrocytic piroplasms.

C. Infections

The cattle were infected by the injection of 1.0 ml of stabilate comprising a suspension of ground up tick infected with *T. parva* (Muguga) in front of the right ear of day 0.

The stabilate is expected to kill cattle around day 18.

D. Treatment

The animals were divided into two groups of 7, one group being kept untreated as controls. The other group was treated with menoctone, formulated in 20% dimethyl sulphoxide (DMSO) and 80% corn oil as a 100 mg/ml mixture. Treatment was commenced on the first day on which the animal had a temperature of at least 39.5° C and schizonts could be found in lymph-node smears. Menoctone was injected intravenously as a single injection of 5 mg/kg on the day the above criteria were satisfied (day 9), and 1 mg/kg intravenously on each of the subsequent 5 days, making a total dose of 10 mg/kg.

E. Results

Treated Group — Injection of menoctone halted the development of infection in all cases, and temperatures had all fallen by the following day. No schizonts were found in their lymph-node smears by day 15. All the treated animals made an uneventful recovery and looked extremely fit at the end of the experiment. They gained an average of 21.5% in weight.

Controls — All animals developed severe theileriosis and 6 of them died between days 15-21. Theileriosis was diagnosed as the cause of death in all cases. The remaining animal was very sick until day 24, then made a gradual recovery until by day 28 it had gained 7.0% in weight.

F. Serology

On day 16 five of the treated heifers had high titres of antibody, while all the untreated calves remained negative. On days 22 and 28 all surviving calves had high titres.

G. Challenge

The eight surviving calves were challenged with *T. parva* (Muguga) stabilate on day 38, as also were 6 control animals. All control animals died whilst the other eight survived, and only in 3 cases did macroschizonts appear with accompanying very mild reaction.

EXAMPLE 2

Prophylactic Trial

A. Experimental animals

Ten susceptible cattle were used for this trial, which were Boran, Charollois and crosses weighing about 200kg each, divided into two groups of 5.

B. Observation

As for Example 1 with additional bi-weekly serological tests.

C. Treatment and Infections

The cattle in the first group were given intravenous injections of menoctone, formulated as in Example 1, of 2.5mg/kg on day 0, followed an hour later by injection of 1ml of stabilate of *T. parva* (Muguga) in front of the left ear. On each of days 1–9 the cattle each received 0.5mg/kg of menoctone intravenously.

The control animals only received the *T. parva* injection.

D. Results

Controls — All five animals developed a classic severe response with three animals eventually dying.

Treated — None of the five animals developed severe symptoms, although two animals showed mild reaction and three had serological responses.

EXAMPLE 3

Therapeutic Trial

A. Experimental Animals

Twenty susceptible high grade cattle were used for this trial each weighing between 100 and 250 kg.

B. Observation

As for Example 1.

C. Treatment and Infections

The cattle were infected by the injection of 1.0 ml of stabilate comprising a suspension of ground up tick infected with *T. Parva* (Kiambu) in front of the right ear on day 0. This particular strain is more virulent than the *T. Parva* strain used in the previous examples.

The animals were divided into four groups of five, one group being kept untreated as controls. Treatment of the remaining groups began on day 2 by which time all the cattle were clearly sick.

Cattle in the first group (i) were given a single intramuscular injection of menoctone, formulated as in Example 1, of 10mg/kg body weight.

Cattle in the second group (ii) were given a single intravenous injection of menoctone, formulated as in Example 1, of 10mg/kg body weight.

Cattle in the third group (iii) received an intravenous injection of menoctone, formulated as in Example 1, of 2.5mg/kg body weight on day 2. On each of days 3 and 7 the cattle each received 0.5mg/kg of menoctone intravenously (total dose 5mg/kg body weight).

The control animals only received the *T. Parva* (Kiambu) injection.

D. Results

Controls — All five animals developed a classic severe response with four animals eventually dying.

Treated:

(i) The intramuscular injection gave immediate control of injection and temperature. The control was maintained and all the cattle made an excellent recovery.

(ii) The intravenous injection gave equally rapid initial control although there were slight relapses in some cases. All cattle made a good recovery.

(iii) None of the five animals developed severe sumptoms although each developed symptoms to a moderate degree. All cattle in the group survived.

PHARMACEUTICAL FORMULATIONS

Example 1.
POUR-ON FOR CATTLE

| | | |
|---|---|---|
| MENOCTONE | 4.0 | Parts by Weight |
| DIMETHYL SULPHOXIDE | 10.0 | Parts by Weight |
| CASTOR OIL | To 100 | Vols. |

Example 2.
AQUEOUS SUSPENSION.

| | | |
|---|---|---|
| MENOCTONE | 1.00 | Parts by Weight |
| NEOSYL | 16.00 | Parts by Weight |
| BENTONITE | 3.20 | Parts by Weight |
| GLYCERIN | 15.00 | Parts by Weight |
| SODIUM BENZOATE | 1.00 | Parts by Weight |
| BEVALOID 35/2 | 1.00 | Parts by Weight |
| THYMOL | 0.04 | Parts by Weight |
| WATER | 62.76 | Parts by Weight |
| | 100.00 | |

Example 3.
SALT BLOCK.

| | | |
|---|---|---|
| MENOCTONE | 0.5 | Parts by Weight |
| SODIUM CHLORIDE | 99.5 | Parts by Weight |

THE FINELY DIVIDED DRUG IS MIXED WITH THE SODIUM CHLORIDE AND THE MIXTURE PRESSED INTO BLOCKS.

Example 4.
PASTE.

| | |
|---|---|
| MENOCTONE | 3.0 |
| GUM TRAGACANTH | 4.0 |
| BEVALOID 35/2 | 1.0 |
| NIPAGIN "M" | 0.1 |
| GLYCERIN | 19.0 |
| WATER | 72.9 |
| | 100.0 |

Example 5.
SUB-CUTANEOUS INJECTION.

| | | |
|---|---|---|
| MENOCTONE | 4.5 | Parts by Weight |
| METHOCEL | 2.0 | Parts by Weight |
| NIPAGIN "M" | 0.1 | Parts by Weight |
| WATER | 93.4 | Parts by Weight |
| | 100.0 | |

Example 6.
INTRAMUSCULAR INJECTION

| | | |
|---|---|---|
| 2-HYDROXY-3-CYCLOHEXYL-1,4-NAPHTHOQUINONE | 9.5 | parts by weight |
| DIMETHYL SULPHOXIDE | 19.0 | parts by weight |
| SORBITON MONOOLEATE | 4.5 | parts by weight |
| CORN OIL | 67.0 | parts by weight |
| | 100.0 | |

Example 7.
As in Example 6 except with menoctone as active ingredient.

What we claim is:

1. A method of treating theileriosis in cattle and sheep both therapeutically and prophylactically, comprising the administration of an effective amount of a compound which is a 2-hydroxy-1,4-naphthoquinone derivative of formula (I) or a pharmaceutically acceptable salt thereof,

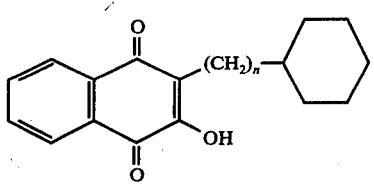

wherein n is zero or 1 to 12, to an animal which is susceptible and infected with or potentially exposed to an infection with *Theileria* species.

2. A method as claimed in claim 1 wherein the value of n is 8 or less.

3. A method as claimed in claim 1 wherein the compound of formula (I) is 2-hydroxy-3-cyclohexyl-1,4-naphthoquinone.

4. A method as claimed in claim 1 wherein the compound of formula (I) is 2-hydroxy-3-(8-cyclohexyloctyl)-1,4-naphthoquinone.

5. A method according to claim 1, wherein the compound of formula (I) or a pharmaceutically acceptable salt thereof is administered at a total dosage of 1 to 20 mg/kg bodyweight over the treatment period.

6. A method according to claim 5, wherein the total dosage is in the range of from 3 to 15mg/kg bodyweight.

7. A method according to claim 6, wherein the total dosage is in the range of from 5 to 10mg/kg bodyweight.

8. A method according to claim 1 wherein the animals to be treated are cattle.

9. A method according to claim 1 wherein the animals to be treated are sheep.

10. A method according to claim 1 wherein the compound of formula (I) or a pharmaceutically acceptable salt thereof is administered as an injectable formulation.

11. A method as claimed in claim 10 wherein the injectable formulation is administered intramuscularly.

12. A method of treating theileriosis in cattle and sheep, comprising the administration of a single dose of a compound of formula (I) or a pharmaceutically acceptable salt thereof as active ingredient, on the day the temperature of the animal rises.

13. A method as claimed in claim 12, wherein the dose of active ingredient is in the range 5 to 10mg/kg bodyweight.

14. A method of preventing theileriosis in cattle and sheep, comprising the repeated administration of a compound of formula (I) or a pharmaceutically acceptable salt thereof as active ingredient, in an effective prophylactic dosage to the apparently healthy animal.

15. A method as claimed in claim 14 wherein a dosage of 0.2 to 5mg/kg bodyweight of active ingredient per administration is administered over a period of from about 4 days to 3 months.

* * * * *